United States Patent [19]

Rieger

[11] Patent Number: 4,846,718
[45] Date of Patent: Jul. 11, 1989

[54] DENTAL PROSTHESIS

[75] Inventor: Klaus Rieger, Hilzingen, Fed. Rep. of Germany

[73] Assignee: Renfert GmbH & Co., Singen, Fed. Rep. of Germany

[21] Appl. No.: 62,491

[22] Filed: Jun. 18, 1987

Related U.S. Application Data

[63] Continuation of Ser. No. 757,532, Jul. 22, 1985, abandoned.

[30] Foreign Application Priority Data

Jul. 26, 1984 [DE] Fed. Rep. of Germany ....... 3427579

[51] Int. Cl.$^4$ ........................................... A61C 13/225
[52] U.S. Cl. ..................................... 433/180; 433/183; 433/218; 433/223
[58] Field of Search ............... 433/180, 181, 182, 183, 433/218, 223

[56] References Cited

U.S. PATENT DOCUMENTS

| 1,033,489 | 7/1912 | Tatham | 433/218 |
| 1,671,781 | 5/1928 | Phillips | 433/183 |
| 2,194,790 | 3/1940 | Gluck | 433/183 |
| 3,344,842 | 10/1967 | Cameron | 433/181 |
| 4,172,323 | 10/1979 | Orlowski | 433/180 |
| 4,516,938 | 5/1985 | Hall | 433/180 |

Primary Examiner—John J. Wilson
Attorney, Agent, or Firm—Bachman & LaPointe

[57] ABSTRACT

A dental prosthesis with a metal body which has an internal cavity open at one end and which is provided with a facing of plastic, ceramic or the like is to be comparatively light and is to be of adequate strength, as well as being able to be used as posts for bridge constructions.

For that purpose it is proposed that the metal body is formed as a carrier element (12) from a filigree grid or lattice having meshes, and is fixedly connected to the facing which surrounds same as a casing layer (10). In addition, two carrier elements (12) formed from the grid or lattice are to be connected by at least one bar (22) and supplemented by a grid or lattice portion (23) cast thereon, to form a bridge construction (21).

1 Claim, 1 Drawing Sheet

U.S. Patent
Jul. 11, 1989
4,846,718
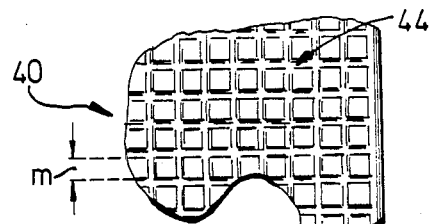
Fig. 4
Fig. 1
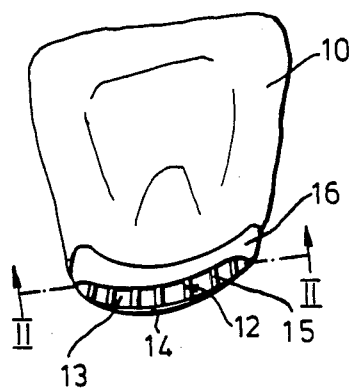
Fig. 2
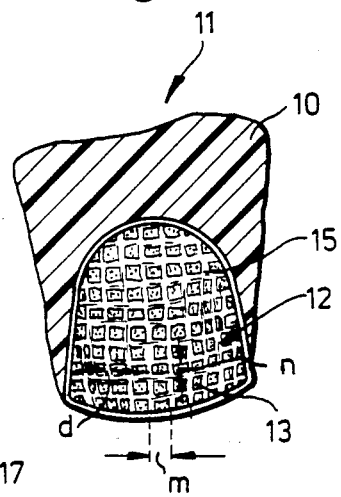
Fig. 3
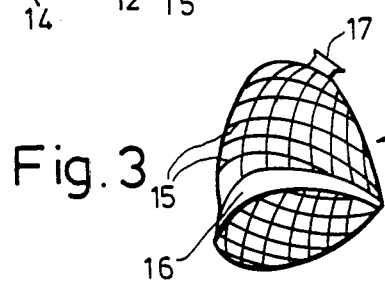
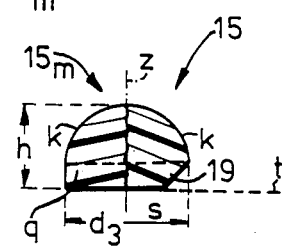
Fig. 5
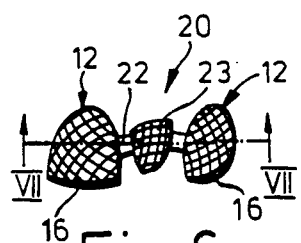
Fig. 6
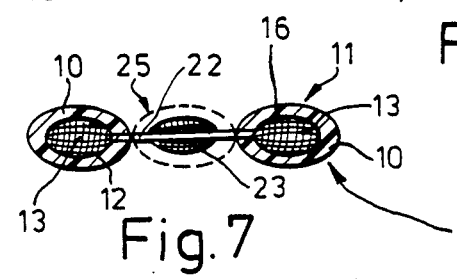
Fig. 7
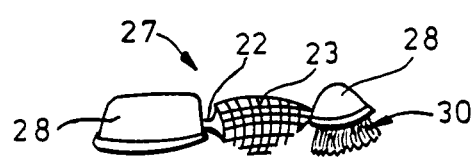
Fig. 8

DENTAL PROSTHESIS

This is a continuation of application Ser. No. 757,532 filed July 22, 1985, now abandoned.

The invention relates to a dental prosthesis comprising a metal body which has an internal cavity that is open at one end, with a facing of plastic material, ceramic or the like. The invention also relates to a method of manufacture thereof.

It is known for a dental prosthesis to be produced from metal and a facing of ceramic or plastic material, for crowning teeth. The advantage of the higher strength of metal is compensated for, when using plastic or porcelain, by the visual aspect and appearance which is closer to the original. For the purposes of manufacturing such a dental prosthesis, a mould which is taken from the stump of the tooth is filled with a molten mass of noble metal, and possibly also non-noble alloys. A thin facing is then applied.

When using such methods, just small errors, which then have a cumulative effect, result in the comparatively heavy dental prosthesis being a poor fit, which gives rise to static problems and problems in regard to the health aspect, more particularly in relation to the adjacent gum.

In addition, when producing bridges, it has been found that solid noble metal alloys give rise to heavy and expensive constructions which are only faced labially or buccally for cosmetic reasons.

Having regard to those considerations, the inventor set himself the aim of providing a method and an apparatus of the kind set forth in the opening part of this specification, which eliminate the disadvantages found and which afford a comparatively light dental prosthesis which is of adequate strength and which can also be used as posts for bridge constructions.

To attain that object, the invention provides that the metal body is formed as a carrier element from a filigree grid or lattice having meshes, and is fixedly connected to the facing which encloses it in the form of a casing layer.

It is also in accordance with the invention that two carrier elements which are formed from the grid or lattice are connected by at least one bar and are supplemented to form a bridge construction by a grid or lattice portion which is cast on said at least one bar. In a construction of poorer quality, each grid or lattice portion may also be cast between two bridge portions which are formed as mesh-less metal caps.

The method according to the invention is distinguished in that a grid or lattice cap, preferably a wax grid or lattice cap, is produced as a pattern from a material which burns without leaving a residue, and is burnt, producing the mould, whereafter a molten metal mass is introduced into the mould and the facing material is built up around the lattice or mesh cap which is formed from the molten metal.

Advantageously, the metal bars of the lattice or grid are of a width or a diameter of from about 0.30 to 0.60 mm, preferably 0.4 mm, while in accordance with a further feature of the invention, the internal width of the meshes of the grid or lattice is about 0.5 to 1.0 mm, preferably 0.7 mm.

The above-indicated dimensions in regard to the grid or lattice and likewise in regard to the pattern for producing the mould cavity therefor ensure on the one hand the required stability, while at the same time being low in weight, while on the other hand also ensuring good translucency of the finished dental prosthesis, which therefore has the ceramic casing, plastic casing or the like.

It has been found desirable for each bar of the lattice or grid structure to have a cross-section of part-cylinder contour, which defines at least a portion of the periphery thereof.

In order to produce a force locking connection between the facing and the grid or lattice basket structure, the grid or lattice bar has at least one undercut region which is disposed on the side remote from the facing. For that purpose, at least one of hte edges of the bar is preferably bevelled or chamferred inwardly.

By virtue of the oxidation process which normally occurs at metal surfaces, an intimate connection is produced between the ceramic casing and the burnable alloy of the carrier cap, without the need for further intermediate layers.

In accordance with a further feature of the invention, in particular in relation to what are known as bridge posts, the carrier cap is thicker in a gum-ward direction, and is possibly also of a multi-layer or multi-ply construction, without thereby having a substantial adverse effect on translucency.

Further advantages, features and details of the invention will be apparent from the following description of preferred embodiments and with reference to the drawings in which:

FIG. 1 is a rear view of a dental prosthesis in the form of a crown, consisting of carrier element and facing, FIG. 2 is a view in longitudinal section through FIG. 1, taken along line II—II therein, FIG. 3 is a perspective view of the carrier element, FIG. 4 is a view of a part of an accessory aid for producing the carrier element, FIG. 5 shows views in cross-section on an enlarged scale through a part of a carrier element, FIG. 6 shows a rear view of a carrier element for a bridge construction, FIG. 7 shows a view in section through FIG. 6, taken along line VII—VII therein, through the carrier element and the facing, and FIG. 8 is a view corresponding to FIG. 6 of another bridge construction.

The ceramic casing 10 of a crown 11 is built up on a carrier element 12 comprising a metal grid or lattice with an internal width in the grid or lattice apertures, referred to hereinafter as the mesh width, as indicated by m and n, of from about 0.6 ×0.6 mm to 1.0×1.0 mm, defining a crown internal cavity 13 with an opening 14 which faces downwardly in FIG. 1.

The diameter d of the metal grid or lattice bars 15 is about 0.3 mm to 0.6 mm. In plan view, the shape of the meshes of the carrier element 12 may be slightly oval, although that is not shown in the drawings for the sake of enhanced clarity thereof.

For the purposes of manufacturing the carrier element 12 which is similar to a small-scale thimble and which is referred to hereinafter as the carrier cap 12, a wax grid or lattice 40 of the described grid form and size is applied to a pattern stump with a thin coating of wax, the wax grid or lattice 40 readily adopting the shape of the outside of the stump, with its wax limb portions 44. A strengthening edge is modelled on what will subsequently be the back of the crown, that is to say, on the lingual side. The wax grid or lattice 40 which undergoes combustion without a residue serves to define a cavity for the metal grid or lattice which is then cast in that form and in which the above-mentioned strengthening edge appears as a part-annular edge rib 16.

The carrier cap 12 produced in that way is shown in FIG. 3 and shows the edge rib 16 at its downwardly facing opening and a casting gate projection 17 which is to be ground off, at its closed upper end.

Opaque fluid is applied to the carrier cap 12, as foundation, and then the ceramic casing 10 is applied as a moist mass. The above-indicated mesh width m and n of the carrier cap 12 prevents ceramic particles from running off during the operation of applying the ceramic material.

By virture of the layer of oxide which is produced on the surface of the grid or lattice, the ceramic material adheres very firmly. The thickness of the layer of ceramic casing 10 on the grid or lattice of the carrier cap 12, which in turn is transparent in the grid or lattice apertures, is considerably greater than in the case of conventional facings so that it provides a translucency which almost corresponds to a natural tooth.

As described, adhesion of the ceramic material to the carrier cap 12 is made possible in part by the layer of oxide on the material, and also the shrinkage of the ceramic material 10 on to the carrier cap 12 during the buring operation. In addition, a surface roughness which can additionally be produced assists, with its engagement cavities or depressions, and in regard to engaging behind projections. When using plastic material for the casing 10, the arrangement only provides a positive or form-locking bond, namely, engagement behind projections.

FIG. 5 shows two embodiments of the cross-section, shown on an enlarged scale, through one of the grid or lattice bars 15; each cross-section, of which half is shown, is supplemented on the other side of an axis of symmetry as indicated by z, by a second half which corresponds in form. Thus, the cross-section of the bar $15_m$, which is on the left in FIG. 5, is defined by a semi-circular contour k and a square or rectangular container q. The total height h of the bar $15_m$ corresponds in this case to the dimension of the width $d_3$, which is also to be referred to as the diameter, being 0.4 mm.

The bar 15 shown by way of example in the right-hand side of FIG. 5 shows that in this case the square or rectangular contour is replaced by a plygonal base contour s which produces an undercut edge portion 19, with reference t indicating a contact or fitting surface.

A carrier element 20 as shown in FIG. 6, for a bridge construction 21, comprises two of the carrier caps 12 which are connected by a bar 22 formed thereon. Carried on the bar 22 is a grid or lattice portion 23. The portion 23 and the carrier caps 12 are thinner in the buccal region that at their rear which is towards the tongue. The carrier caps 12, of grid or lattice form, are stable and desirably low-strength holding means which, for an intermediate crown 25 which in turn is built up on the grid portion 23, are fitted on to tooth stumps 30 (see FIG. 8).

All in all, this also provides a considerable reduction in weight in comparison with a conventional dental prosthesis, with at the same time a saving of material, which cuts costs.

The bridge construction 27 shown in FIG. 8 comprises two metal caps 28, on the connecting bar 22 of which is carried a grid or lattice portion 23. In comparison with the embodiment shown in FIG. 6, the weight in this case is higher, but, by virtue of the lattice portion 23, lower than in the case of conventional bridge constructions.

I claim:

1. A lightweight dental prosthesis which comprisse an internal carrier element supporting an exterior casing, said carrier element defining a thimble-shaped metallic mesh or lattice bounded in part by an edge rib for increasing strength, said carrier element having been cast from a mold created by the lost wax process and said exterior casing defining a relatively thick layer of generally translucent material, said mesh defining a plurality of intersecting bars, portions of selected bars being bevelled or chamfered to create a locking connection between said carrier element and said casing layer.

* * * * *